United States Patent
Holtzman Gazit et al.

(10) Patent No.: US 12,322,112 B2
(45) Date of Patent: Jun. 3, 2025

(54) METHODS AND APPARATUSES FOR VISUALIZATION OF TUMOR SEGMENTATION

(71) Applicant: Novocure GmbH, Root (CH)

(72) Inventors: Michal Holtzman Gazit, Haifa (IL); Reuven Ruby Shamir, Haifa (IL)

(73) Assignee: Novocure GmbH, Baar (CH)

( * ) Notice: Subject to any disclaimer, the term of this patent is extended or adjusted under 35 U.S.C. 154(b) by 508 days.

(21) Appl. No.: 17/683,643

(22) Filed: Mar. 1, 2022

(65) Prior Publication Data

US 2022/0284585 A1  Sep. 8, 2022

Related U.S. Application Data (60) Provisional application No. 63/155,564, filed on Mar. 2, 2021, provisional application No. 63/155,626, filed on Mar. 2, 2021.

(51) Int. Cl.
*G06T 7/11* (2017.01)
*G06T 7/136* (2017.01)

(52) U.S. Cl.
CPC ............... *G06T 7/11* (2017.01); *G06T 7/136* (2017.01); *G06T 2207/20081* (2013.01); *G06T 2207/30096* (2013.01)

(58) Field of Classification Search
CPC ............ G06T 7/11; G06T 2207/20081; G06T 2207/30096; G06T 2207/20084
See application file for complete search history.

(56) References Cited

U.S. PATENT DOCUMENTS

| | | | |
|---|---|---|---|
| 7,565,205 B2 | 7/2009 | Palti | |
| 11,464,491 B2 * | 10/2022 | Jacob | G16H 30/40 |
| 2010/0322489 A1 * | 12/2010 | Tizhoosh | G06T 7/174 |
| | | | 345/157 |
| 2015/0327766 A1 * | 11/2015 | Gupta | G06T 7/90 |
| | | | 600/407 |
| 2019/0026897 A1 * | 1/2019 | Wu | G06T 11/005 |

(Continued)

FOREIGN PATENT DOCUMENTS

CN  110517759 A  11/2019

OTHER PUBLICATIONS

Spyridon Bakas, et al., "Identifying the best machine learning algorithms for brain tumor segmentation, progression assessment, and overall survival prediction in the Brats challenge", (2019), 49 pages.

(Continued)

*Primary Examiner* — Bobbak Safaipour
*Assistant Examiner* — Michael Kim Maiden
(74) *Attorney, Agent, or Firm* — McCarter & English, LLP; Michael A. Sartori (57) ABSTRACT

A computer-implemented method for tumor segmentation, the method comprises obtaining image data of a region of interest of a subject's body, wherein the region of interest corresponds to a tumor of the subject's body, generating two or more tumor segmentation predictions based on the image data, calculating a divergence between the two or more tumor segmentation predictions, and generating a visualization of tumor segmentation uncertainty based on the calculated divergence between the two or more tumor segmentation predictions.

20 Claims, 4 Drawing Sheets
(2 of 4 Drawing Sheet(s) Filed in Color)

(56) References Cited

U.S. PATENT DOCUMENTS

| | | | |
|---|---|---|---|
| 2020/0167930 A1* | 5/2020 | Wang | G06N 3/08 |
| 2020/0219261 A1* | 7/2020 | Shamir | G06T 7/10 |
| 2022/0036135 A1 | 2/2022 | Hu et al. | |

OTHER PUBLICATIONS

Matthew T. Ballo, et al., "Correlation of Tumor Treating Fields Dosimetry to Survival Outcomes in Newly Diagnosed Glioblastoma: A Large-Scale Numerical Simulation-Based Analysis of Data from the Phase 3 EF-14 Randomized Trial," Int J Radiat Oncol Biol Phys, vol. 104, No. 5, (2019), 1106-1113.

Ken Chang, et al., "Automatic assessment of glioma burden: a deep learning algorithm for fully automated volumetric and bidimensional measurement," Neuro-Oncology, 21(11), (2019), pp. 1412-1422.

Filipe R. Cordeiro, et al., "A survey on deep learning with noisy labels: How to train your model when you cannot trust on the annotations?", 33rd SIBGRAPI Conference on Graphics, Patterns and Images (SIBGRAPI), (2020), 8 pages.

James S. Cordova, et al., "Quantitative tumor segmentation for evaluation of extent of glioblastoma resection to facilitate multisite clinical trials", Translational Oncology, vol. 7, No. 1, (Feb. 2014), pp. 40-47.

Ekin Ermis et al., "Fully automated brain resection cavity delineation for radiation target volume definition in glioblastoma patients using deep learning", Radiation Oncology, 15:100 (May 2020), 10 pages.

Bo Han et al., "Co-teaching: Robust training of deep neural networks with extremely noisy labels", In: NeurIPS, (2018), 13 pages.

Christian Henker, et al., "Volumetric quantification of glioblastoma: experiences with different measurement techniques and impact on survival," J. Neurooncol, 135, (2017), pp. 391-402.

Davood Karimi et al., "Deep learning with noisy labels: Exploring techniques and remedies in medical image analysis", Medical Image Analysis 65, 101759 (2020), 49 pages.

Diederik P. Kingma et al., "Adam: A method for stochastic optimization," ICLR 2015, (2015), pp. 1-15.

Eilon D. Kirson, et al., "Alternating electric fields arrest cell proliferation in animal tumor models and human brain tumors", PNAS, vol. 104, No. 24, (2007), pp. 10152-10157.

Sangjune Lee, et al., "Improved dosimetric accuracy with semi-automatic contour propagation of organs-at-risk in glioblastoma patients undergoing chemoradiation," Journal of Applied Clinical Medical Physics 20:12, (2019), pp. 45-53.

Raghav Mehta, et al., "Uncertainty evaluation metric for brain tumour segmentation," Medical Imaging with Deep Learning, (2020), 8 pages.

Raphael Meier et al., "Patient-specific semi-supervised learning for postoperative brain tumor segmentation," Medical Image Computing and Computer-Assisted Intervention—MICCAI 2014. vol. 17, (2014), pp. 714-721.

Bjoern H. Menze, et al., "The multimodal brain tumor image segmentation benchmark (Brats)", IEEE Transactions on Medical Imaging vol. 34, No. 10, (2015), pp. 1993-2024.

Andriy Myronenko, "3D MRI brain tumor segmentation using autoencoder regularization," (2019), 10 pages.

Tanya Nair et al., "Exploring uncertainty measures in deep networks for multiple sclerosis lesion detection and segmentation", Medical Image Computing and Computer Assisted Intervention—MICCAI 2018, Springer International Publishing, (2018), 9 pages.

Adam Paszke et al., "Pytorch: An imperative style, high-performance deep learning library," 33rd Conference on Neural Information Processing Systems (NeurIPS 2019), (2019), 12 pages.

Mengye Ren et al., "Learning to reweight examples for robust deep learning," 35th ICML (2018), 13 pages.

Olaf Ronneberger, et al., "U-net: Convolutional networks for biomedical image segmentation," Medical Image Computing and Computer-Assisted Intervention—MICCAI 2015, (2015), 8 pages.

Hongxin Wei, et al., "Combating noisy labels by agreement: A joint training method with co-regularization," In: Proceedings of the IEEE/CVF Conference on Computer Vision and Pattern Recognition (CVPR), (2020), 11 pages.

Steven V. Weijs et al., "Kullback-Leibler divergence as a forecast skill score with classic reliability-resolution-uncertainty decomposition", American Meteorological Society, Monthly Weather Review, vol. 138, (2010), pp. 3387-3399.

Guotai Wang et al., "Aleatoric uncertainty estimation with test-time augmentation for medical image segmentation with convolutional neural networks," Feb. 1, 2019, 13 pages.

Alain Jungo et al., "Towards Uncertainty-Assisted Brain Tumor Segmentation and Survival Prediction," 2018, pp. 474-485.

Alex Kendall et al., "Bayesian SegNet: Model Uncertainty in Deep Convolutional Encoder-Decoder Architectures for Scene Understanding," Oct. 10, 2016, 11 pages.

Tanya Nair et al., "Exploring Uncertainty Measures in Deep Networks for Multiple Sclerosis Lesion Detection and Segmentation," Oct. 16, 2018, 15 pages.

Moloud Abdar et al., "A Review of Uncertainty Quantification in Deep Learning: Techniques, Applications and Challenges," Jan. 6, 2021, 68 pages.

* cited by examiner

*(org)*
FIG. 3A

*(baseline)*
FIG. 3B

*(SD)*
FIG. 3C

*(manual)*
FIG. 3D

*(org)*
FIG. 3E

*(manual)*
FIG. 3H

*(org)*
FIG. 3I

*(manual)*
FIG. 3L

*(manual)*
FIG. 3P

METHODS AND APPARATUSES FOR VISUALIZATION OF TUMOR SEGMENTATION

CROSS-REFERENCE TO RELATED APPLICATIONS

This application claims priority to the U.S. Provisional Application No. 63/155,564, filed Mar. 2, 2021 and U.S. Provisional Application No. 63/155,626 filed Mar. 2, 2021, both of which are incorporated herein by reference.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into a region of interest by transducers placed directly on the patient's body and applying AC voltages between the transducers. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

TTFields treatment planning can include the segmentation of tissues on medical images (e.g., MR images) for evaluating the distribution of TTFields and the quantitative treatment efficacy. Manual segmentation is time-consuming and often requires, for example, 20-50 minutes for a highly skilled and experienced annotator to perform. Furthermore, the large amounts of data and data annotations result in noisy labeling and intra- and inter-observer variability.

SUMMARY OF THE INVENTION

One aspect of the invention is directed to a computer-implemented method for tumor segmentation, the method comprises obtaining image data of a region of interest of a subject's body, wherein the region of interest corresponds to a tumor of the subject's body, generating two or more tumor segmentation predictions based on the image data, calculating a divergence between the two or more tumor segmentation predictions, and generating a visualization of tumor segmentation uncertainty based on the calculated divergence between the two or more tumor segmentation predictions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Methods and apparatuses for tumor segmentation and uncertainty visualization are disclosed. Given an image of a subject's body with a tumor, the inventive computer-based techniques segment the tumor in the image, provide an uncertainty measure of the segmentation, and provide visualizations of the tumor segmentation and the uncertainty measurement. The segmentation of the image is determined by trained segmentation networks. Surgical data and/or anatomical data may be included to improve the segmentation of the image.

The disclosed techniques can be utilized for surpassing inter-observer variability, and the user can edit the segmentation according to an uncertainty level. In certain embodiments, the disclosed techniques use segmentation networks that are co-trained together to cope with noisy labels and inter-observer variability. In one example, the Kullback-Leibler (KL) divergence can be used to visualize the segmentation uncertainty. As various human annotators may segment the same object differently, the inventors realized that techniques for confidentially editing the segmentation results are needed. Using the inventive computer-based segmentation disclosed herein, a visualization of the segmentation uncertainty is provided and can be utilized to improve the trust of human annotators.

The disclosed systems and methods for segmentation can be used for planning TTFields treatment and other clinical applications. In non-limiting embodiments, the disclosed systems and methods for segmentation of tumors (e.g., glioblastoma multiforme ("GBM")) can be used for post-operative patients. In one example, a surgery type and non-tumorous tissue delineation can be integrated to automatically segment the tumor. The disclosed segmentation techniques can be extended with surgery-type, anatomical information, and uncertainty visualization to facilitate an accurate segmentation of postoperative GBM.

The disclosed techniques may outperform other segmentation methods for postoperative data. In one example, the disclosed techniques may reduce resection-cavity and necrotic-core segmentation errors. As manual annotation for the images can be subject to expert disagreement, the disclosed techniques may provide an uncertainty map coupled with the segmentation result. This may allow visualization and fast editing of the tissues to improve the results that are dependent on user preference.

Figure 1:
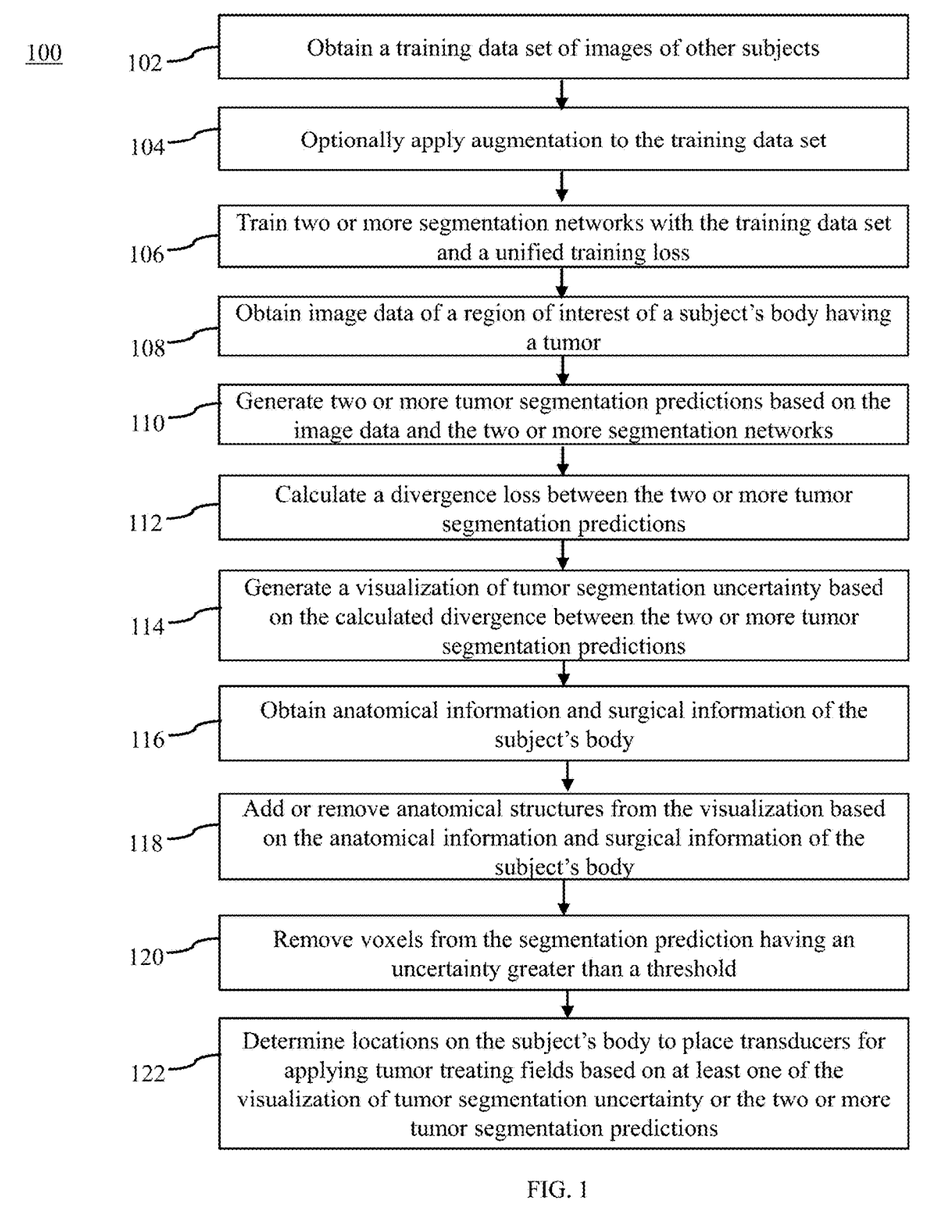
FIG. 1 depicts an example computer-implemented method of tumor segmentation.
Figure 2:
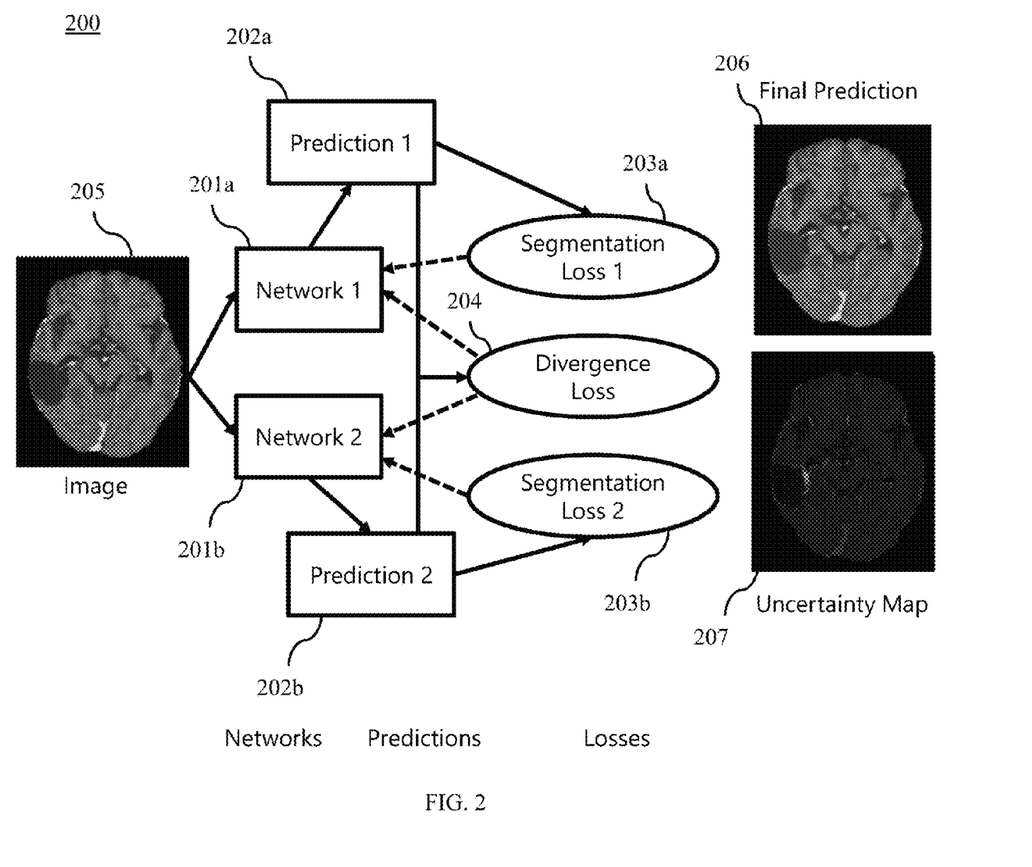
FIG. 2 depicts an example of a computer-based architecture for tumor segmentation and uncertainty visualization.

FIG. 1 depicts an example computer-implemented method 100 of tumor segmentation and uncertainty visualization, and FIG. 2 depicts an example of a computer-based architecture 200 for tumor segmentation and uncertainty visualization. For non-limiting illustration purposes, the steps of method 100 in FIG. 1 are discussed with respect to the example architecture 200 in FIG. 2.

At step 102, a training data set of images of other subjects may be obtained from a computer-readable medium. The training data set of images may include any medical images. For example, the training data set may include images of x-rays, computed tomography (CT) scan, magnetic resonance imaging (MRI), ultrasound, nuclear medicine imaging, positron-emission tomography (PET), arthrogram, myelogram, or a combination thereof. In developing the training set, trained human annotators may segment the tumors according to the predetermined labels (e.g., resection, necrotic core, and enhancing tumor). The resulting training set may be stored on a computer-readable medium.

At step 104, augmentation may be optionally applied to the training data set. The augmentation can include at least one of intensity normalization, random shift, random scale-up of intensity value, random flip, or random scaling of an image patch. In one example, the medical images can be resampled (e.g., to 1 mm$^3$ voxel resolution). In non-limiting embodiments, a bias field correction and/or skin and skull stripping can be applied as a pre-process. In one example, a patch size of 128×128×128 voxels can be used, and the following augmentation can be applied to the data samples to increase the variability and improve model robustness: intensity normalization, random shift up to 0.1, random scale up to 10% of intensity values, random flip and random scaling of ±10% of the image patch.

At step 106, two or more segmentation networks 201a, 201b may be trained with the training data set and a unified training loss. Each of the segmentation networks 201a, 201b can include, for example, a variational auto-encoder that reconstructs the image data from a shared encoder parameter. In non-limiting embodiments, the disclosed method can include obtaining two or more segmentation networks 201a, 201b trained using a common training set with a plurality of training losses.

In certain embodiments, the segmentation networks 201a, 201b output predictions 202a, 202b and can be trained in parallel using the predictions 202a, 202b and a unified loss. The unified loss can include at least one of segmentation loss 203a, 203b, reconstruction loss, or divergence loss 204. In non-limiting embodiments, the unified loss can include a parameter to balance the segmentation loss 203a, 203b and the divergence loss 204. In one example, the segmentation loss 203a, 203b can include a Dice coefficient, a cross-entropy loss, or a combination thereof. In one example, the divergence loss 204 can include a Kullback-Leibler (KL) divergence loss. In certain embodiments, the segmentation networks 201a, 201b can be trained using the augmented training data set. In one example, the segmentation networks 201a, 201b can be trained using PyTorch and MONAI with Adam optimizer and epochs (e.g., 200 epochs). The learning rate can be initially set to 1e-4 and be reduced whenever the metric comes to a plateau of 10 epochs. The two or more segmentation networks 201a, 201b can be simultaneously trained. These segmentation networks 201a, 201b can have an identical architecture but differ in their parameters. Each segmentation network 201a, 201b can have its own segmentation loss with respect to the ground truth labels. A divergence loss 204 between the predictions 202a, 202b of the segmentation networks 201a, 201b can be calculated so that the entire system is jointly trained and updated.

As an example, the unified training loss (or total training loss) for a given sample $x_i$ can be calculated as follows:

$$L_{Total} = (1-\lambda)L_{seg}(x_i, y_i) + \lambda L_{div}(x_i) + \beta L_{rec} \quad (1)$$

where $\lambda$ is a parameter that balances between the individual segmentation loss (203a, 203b), $L_{seg}$, and the divergence loss (204), $L_{div}$. In one example, $\lambda$ can be set to 0.1. In non-limiting embodiments, a reconstruction loss, $L_{rec}$, of the auto-encoder can be added for each segmentation network 201a, 201b to the calculation of $L_{Total}$. $L_{rec}$ is the $L_2$ loss between input and reconstructed images. The weight $\beta$ can be set to 0.1.

In one example, the segmentation loss 203a, 203b can be a combination of Dice coefficient and Cross-Entropy as follows:

$$L_{seg} = \sum_{k=1}^{K}((1-\alpha)L_{Dice}(p_k(x_i), y_i) + \alpha L_{CE}(p_k(x_i), (y_i)) \quad (2)$$

where K is the number of segmentation networks 201 (e.g., set to 2). $p_k$ is the prediction output of each network. $\alpha$ is used to balance between Dice and cross-entropy loss (e.g., set to 0.3). In non-limiting embodiments, the two different segmentation networks 201a, 201b can agree on prediction in the correct labels and disagree on incorrect ones. Therefore, the co-regularization term can guide the segmentation networks 201a, 201b to a more stable model for clean labels.

In one example, the divergence loss 204 measures the match between the segmentation predictions 202a, 202b of the segmentation networks 201a, 201b and co-regularizes both segmentation networks 201a, 201b. A symmetric Kullback-Leibler (KL) divergence loss 204 can be calculated as follows:

$$L_{div} = D_{KL}(p_1 \| p_2) + D_{KL}(p_2 \| p_1) \quad (3)$$

To properly handle noisy labels, the small-loss criterion techniques can be performed. This criterion is based on the idea that small loss samples are more likely to be correctly labeled. Therefore, in each mini-batch, the voxels can be sorted according to their joint loss given in Equation (1) and averaged over a part of the voxels P with the smallest values. This way, the noisy labeled voxels have a lesser effect on the total loss and the back-propagation update. P may be the presumed percentage of correctly labeled samples in the dataset. The small-loss criterion can be utilized for the divergence and cross-entropy losses that are calculated voxel-wise.

At step 108, image data 205 of a region of interest of a subject's body having a tumor can be obtained. In one example, the image data of the region of interest can include data of x-rays, computed tomography (CT) scan, magnetic resonance imaging (MRI), ultrasound, nuclear medicine imaging, positron-emission tomography (PET), arthrogram, myelogram, or a combination thereof. Inter-observer variability/difference may be observed from the image data. In one example, differences in training and image quality may increase the inter-observer variability. As the Dice score between the model's prediction and ground truth annotation can be limited by the inter-observer score, the disclosed techniques consider the presence of noisy labels and provide segmentation methods without requiring a clean annotated dataset. To overcome noisy labels and inter-observer variability in the dataset and to facilitate an interactive visual review of the segmentation result, the uncertainty can be calculated by agreement maximization.

At step 110, two or more tumor segmentation predictions 202a, 202b may be generated based on the image data 205 and the two or more segmentation networks 201a, 201b.

At step 112, the divergence loss 204 can be calculated between the two or more tumor segmentation predictions 202a, 202b generated by the two or more segmentation networks 201a, 201b.

At step 114, a visualization of tumor segmentation uncertainty can be generated based on the calculated divergence loss 204 between the two or more tumor segmentation predictions 202a, 202b. In one example, the visualization can include an image of the subject with a segmentation prediction 206 and/or an uncertainty map 207. The uncertainty map 207 can be based on the calculated divergence loss 204 between the two or more tumor segmentation predictions 202a, 202b. The KL divergence, a relative entropy between two probability distributions, can be calculated as the uncertainty between the segmentations predictions 202a, 202b. To visualize the uncertainty, the KL divergence between the baseline networks predictions 202a, 202b can be calculated using Equation (3). The uncertainty values can be normalized over the dataset, such that the maximum uncertainty is set to 1 and the minimum is set to 0. Then, the uncertainty map 207 can be generated as a heat map on top of the segmentation.

In non-limiting embodiments, the uncertainty map 207 can be used to remove voxels that are associated with high uncertainty from the segmentation map 206, with a user-defined threshold. In non-limiting embodiments, the visualization of the region of interest of the subject's body includes uncertainty estimation as to the generated postoperative tumor segmentation of the subject's body.

At step 116, anatomical information and surgical information of the subject's body can be obtained. In non-limiting embodiments, the tumor segmentation predictions 202a, 202b can be generated based on the image data 205, the anatomical information, and/or the surgical information. In one example, image data 205 of a region of interest, anatomical information, and surgical information of the subject's body can be obtained, where the region of interest may correspond to a postoperative region of a tumor of the subject's body. The postoperative tumor segmentation and/or visualization of the subject's body can be generated based on the image data, the anatomical information, and the surgical information.

At step 118, anatomical structures may be added or removed from the visualization based on the anatomical information and surgical information of the subject's body. By adding or removing the anatomical structures, the disclosed techniques can improve the segmentation performance. For example, several issues that affect the segmentation performance for postoperative GBM can be addressed (e.g., interchange of necrotic core and resection and/or interchange of CSF and resection).

The error caused by the interchange of necrotic core and resection may be related to the similar appearance of necrotic core and resection in some of the images. The disclosed techniques may reduce this error by incorporating the surgery type into the prediction results as a post-process. If the patient underwent a biopsy, there is no resection in the image. If the patient had a grand-total resection (GTR), the necrotic core is entirely evacuated. For the post-processing of the segmentation results, if the surgery type is the biopsy, the resection labeled voxels can change to necrotic core. In the case of GTR surgery, the necrotic core voxels can change to resection.

The error caused by the interchange of CSF and resection can be observed when the resection cavity is adjacent to the CSF. To solve this issue, the disclosed techniques include segmenting the CSF in addition to the tumor tissues. The disclosed dataset can include validated CSF labels that can be utilized to train the segmentation networks 201a, 201b. Co-segmentation of the CSF by the disclosed techniques may reduce mislabeling of resection cavity voxels.

At step 120, voxels from the segmentation prediction having an uncertainty greater than a threshold may be removed. The threshold may be a user-defined threshold.

At step 122, locations on the subject's body to place transducers for applying TTFields may be determined based on at least one of the visualization of tumor segmentation uncertainty or the two or more tumor segmentation predictions 202a, 202b. In one example, the uncertainty map 207 may be generated based on the visualization of tumor segmentation uncertainty and/or the two or more tumor segmentation predictions 202a, 202b. The uncertainty map 207 may highlight the regions that require careful examination. For example, the mean KL divergence can be overlaid as a heat map on top of the medical image of the target tissue. The uncertainty map 207 can mark the most uncertain areas.

In certain embodiments, the TTFields can include predetermined parameters. As an example, the TTFields may include an intensity within an intensity range from about 1 V/cm to about 20 V/cm. As an example, the TTFields can include a frequency within a frequency range from about 50 kHz to about 1 MHz. Other possible exemplary parameters for the TTFields may include active time, dimming time, and duty cycly (all of which may be measured in, for example, ms units), among other parameters.

In some embodiments, an apparatus for tumor segmentation and uncertainty visualization may be provided. In one example, the apparatus may include one or more processors and memory storing processor-executable instructions that, when executed by the one or more processors, cause the apparatus to execute the disclosed methods for tumor segmentation and/or uncertainty visualization.

In some embodiments, a transducer for applying an alternating electric field with predetermined parameters to the subject's body may be provided. The alternating electric field can be applied based on at least one of visualization of tumor segmentation uncertainty or the segmentation prediction.

In some embodiments, the disclosed system may include a computer-based architecture for tumor segmentation and uncertainty visualization. As an example, FIG. 2 depicts an example of a computer-based architecture for tumor segmentation and uncertainty visualization. The computer-based architecture may incorporate a segmentation agreement loss to regularize two or more baseline models that are trained simultaneously. The agreement loss may be utilized to visualize the segmentation uncertainty. In non-limiting embodiments, the computer-based architecture may include a variation of Unet. For example, the computer-based architecture may incorporate a variational auto-encoder that reconstructs an MRI image from the shared encoder parameters for regularization. In non-limiting embodiments, the computer-based architecture may be designed for segmentation (e.g., preoperative GBM segmentation) and may incorporate multiple modalities. To improve the accuracy of the segmentation, the computer-based architecture may incorporate anatomical and/or surgical information. For example, the data may include medical images (e.g., MRI scans) of various types of surgery (e.g., grand total resection of the tumor, partial resection, and biopsy of the tumor).

In certain embodiments, two or more segmentation networks can be jointly trained using a unified loss consisting of segmentation loss and divergence loss. For different tumor tissue, other anatomical structures can be added to overcome confusion with healthy tissue.

In certain embodiments, the image data can be resampled. For example, the medical images can be resampled to 1 mm$^3$ voxel resolution. As a pre-process, a bias field correction and skin/skull stripping can be applied.

In certain embodiments, various augmentations can be applied to the data sample to increase the variability and improve model robustness. For example, during training, a patch of voxels (e.g., 128×128×128) can be used, and the following augmentation can be applied to the data samples to increase the variability and improve model robustness: intensity normalization, random shift (e.g., up to 0.1), random scale up (e.g., to 10% of intensity values), random flip, and/or random scaling of ±10% of the image patch. A balance can be ensured between patches that contain the tumor and those without it.

In certain embodiments, an improved Dice coefficient and false discovery rate (FDR) may be provided. For example, a network (e.g., Resnet-VAE network) can be trained on a training dataset with a combination of Dice and Cross-Entropy loss and certain labels (e.g., resection, necrotic core, and enhancing tumor). In non-limiting embodiments, surgical information, as a post-process of the Resnet-VAE, can be added to reduce the segmentation error.

Experimental Results

Using certain embodiments disclosed herein, a set of 340 labeled T1 enhanced MRI brain scans of postoperative GBM patients were divided into 270 training images and 70 images testing images. These images were all re-sampled to 1 mm$^3$ voxel resolution. As a pre-process, a bias field correction and skin and skull stripping were applied. During training, a patch size of 128×128×128 voxels was used, and the following augmentation on the data samples was applied to increase the variability and improve model robustness: intensity normalization; random shift up to 0:1; random scale up to 10% of intensity values; random flip; and random scaling of ±10% of the image patch. A balance was ensured between patches that contain the tumor and those without the tumor. Two segmentation networks were trained using PyTorch and MONAI with Adam optimizer and 200 epochs. The learning rate was initially set to 1e-4 and reduced whenever the metric came to a plateau of 10 epochs.

Next, a Resnet-VAE network was trained using the training postoperative GBM tumors dataset with a combination of Dice and Cross Entropy loss and three labels: (1) resection; (2) necrotic core, and; (3) enhancing tumor. Then, the Resnet-VAE was evaluated on the testing dataset. Next, surgical information was incorporated as a post-process of the Resnet-VAE to reduce the segmentation error and was evaluated on the testing dataset.

Table 1 provides Quantitative Dice data, and Table 2 provides false discovery rate (FDR) data. In Table 1, the "res" column is the Quantitative Dice data for the resection label, the "nec" column is the Quantitative Dice data for the necrotic core label, the "enh" column is the Quantitative Dice data for the enhancing tumor label, and the "wt" column is the Quantitative Dice data for the whole tumor label. In Table 2, the "csf as res" column is the FDR data for CSF being segmented and labeled as resection, the "nc as res" column is the FDR data for necrotic core being segmented and labeled as resection, and the "res as nc" column is the FDR data for resection being segmented and labeled as necrotic core.

Further, in Tables 1 and 2, the "BL" row is data for a single (i.e., baseline) segmentation network. The "SD" row is data for post-processing with surgical data. The "AD" row is data from training with the CSF label. The "UR" row is data from joint training of two segmentation networks with both anatomical data and surgical data and uncertainty regularization. The "UR*" row is the same as the "UR" row but with the removal of uncertain voxels according to user preference.

As shown in Table 1, the Dice is improved (larger values are better), especially in the case of confusion between necrotic core and resection. Moreover, as shown in Table 2, the FDR in the tissues of necrotic core and resection is reduced (smaller values are better).

TABLE 2

|  | csf as res | nc as res | res as nc |
| --- | --- | --- | --- |
| BL | 0.485 | 0.392 | 0.483 |
| SD | 0.132 | 0.079 | 0.080 |

TABLE 2-continued

|  | csf as res | nc as res | res as nc |
| --- | --- | --- | --- |
| AD + SD | 0.049 | 0.059 | 0.075 |
| UR | 0.06 | 0.06 | 0.068 |
| UR* | 0.041 | 0.058 | 0.062 |

TABLE 1

|  | res | nec | enh | wt |
| --- | --- | --- | --- | --- |
| BL | 0.56 | 0.50 | 0.65 | 0.79 |
| SD | 0.62 | 0.59 | 0.65 | 0.79 |
| AD + SD | 0.68 | 0.60 | 0.64 | 0.79 |
| UR | 0.65 | 0.60 | 0.64 | 0.78 |
| UR* | 0.67 | 0.62 | 0.65 | 0.79 |

In some cases, the resection automatic segmentation "leaked" into the ventricle. To handle this issue, the segmentation networks were trained using an additional label (i.e., CSF). The results on the testing dataset are given in the third "AD+SD" row of Tables 1 and 2. Both, the Dice and the FDR are dramatically improved when applying this scheme together with the prior of surgical data. These results demonstrate the importance of adding surgical and anatomical data to the training and post-training process.

Finally, the segmentation networks were trained with uncertainty regularization using Equation (1). Then, user-defined thresholds were simulated to demonstrate that the uncertainty map facilitates segmentation's revision. The results of final segmentation without uncertain voxels removal and with simulated user-defined thresholds are given in Tables 1 and 2 in the fourth "UR" row and the fifth "UR*" row, respectively. Using the inventive techniques, the rate of mislabeled voxels is the lowest compared to all other methods, and the Dice is also improved for enhancing tumor and necrotic core. The uncertainty map highlights the regions that require a careful examination (e.g., FIG. 3K). Furthermore, the simulated user-defined threshold exhibits that the uncertainty map can be utilized to revise the segmentation and reduce mislabeled voxels.

As a note, while the images in the dataset were segmented by a specific human annotator, another human annotator may consider these mislabeled voxels as correct. As such, a user-defined threshold may be employed as disclosed herein to generate a satisfactory result. Therefore, the human annotator can easily edit the computer-generated segmentation based on the computer-generated uncertainty map. Providing the human annotator with some control over the computer-generated segmentation results may help to improve trust in the computer-generated segmentation results and may facilitate the expression of personal preferences in the inter-observer variability space.

Figure 3A:
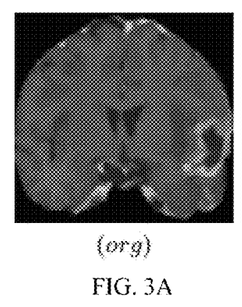
FIGS. 3A-3P depict example results for different aspects of tumor segmentation.
Figure 3B:
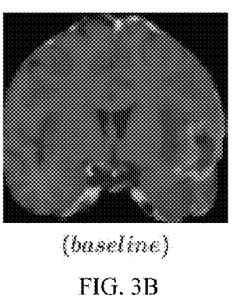
Figure 3C:
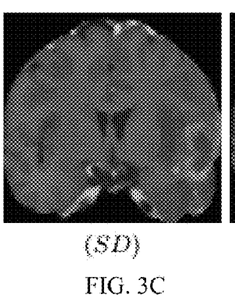
Figure 3D:
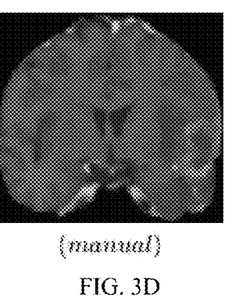
Figure 3E:
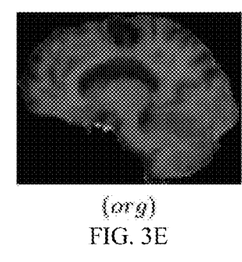
Figure 3F:
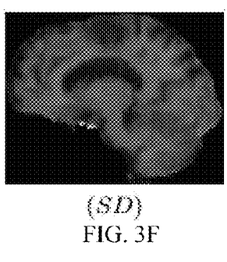
Figure 3G:
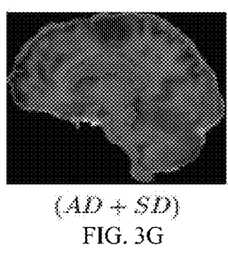
Figure 3H:
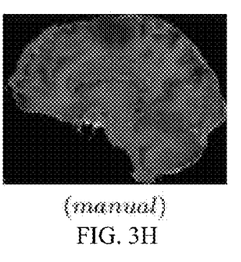
Figure 3I:
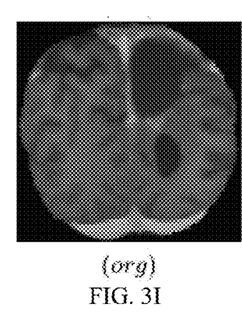
Figure 3J:
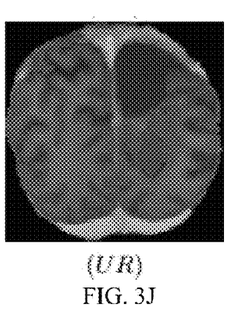
Figure 3K:
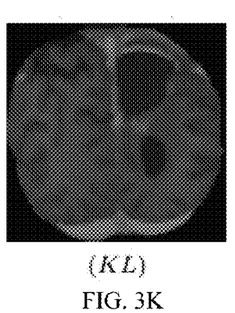
Figure 3L:
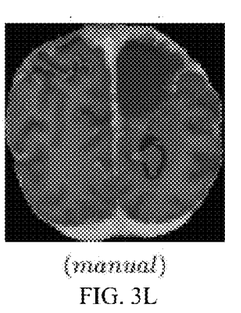
Figure 3M:
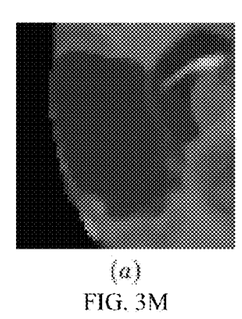
Figure 3N:
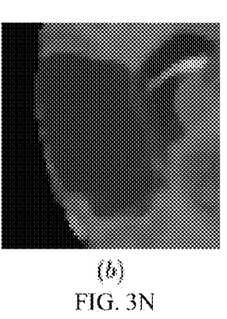
Figure 3O:
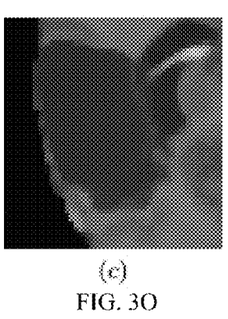
Figure 3P:
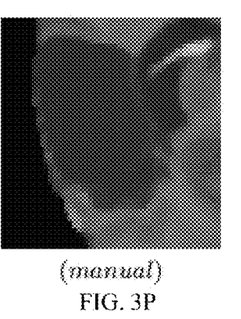

FIGS. 3A-3P (collectively referred to as FIG. 3) depict example experimental results for different aspects of tumor segmentation according to various embodiments. The images in FIG. 3 depict color-coded segmentation results, namely red identifies "resection", green identifies "necrotic", blue identifies "enhancing", and yellow identifies "cerebrospinal fluid (CSF)".

The first row in FIG. 3 (FIGS. 3A-3D) are images comparing the baseline model with surgical data (SD) post process. The first row shows a comparison of the baseline segmentation to the post-process with surgical data. FIG. 3A is the original image. FIG. 3B is the baseline image obtained using certain embodiments, but which includes an error in the necrotic core segment (in green) that is mislabeled as resection (in red). In FIG. 3C, using certain embodiments, this label is corrected to the necrotic core after incorporating the surgical data ("SD"). FIG. 3D is the image with manual segmentation. In comparing the image in FIG. 3C obtained using certain embodiments with the image in FIG. 3D obtained using manual segmentation, the two images are nearly identical.

The second row in FIG. 3 (FIGS. 3E-3H) are images demonstrating the additions of anatomical structure (namely CSF) to the segmentation. The second row demonstrates the result of adding the CSF label (in yellow) to the training of the segmentation networks. FIG. 3E is the original image. FIG. 3F is the image obtained using certain embodiments by segmenting and adding surgery type information. Adding the surgery type information, however, is insufficient since part of the CSF is wrongfully labeled with a resection label (red). As shown in FIG. 3G, this is corrected when segmenting is performed on the CSF in addition to the tumor. FIG. 3H is the image with manual segmentation. In comparing the image in FIG. 3G obtained using certain embodiments with the image in FIG. 3H obtained using manual segmentation, the two images are nearly identical.

The third row in FIG. 3 (FIGS. 3I-3L) are images showing the results of uncertainty regularization with the KL divergence as uncertainty. The third row of FIG. 3 demonstrates an example result of the entire algorithm. FIG. 3I is the original image. FIG. 3J depicts the segmentation result of the co-trained networks. FIG. 3K depicts the mean KL divergence overlaid as a heat map on top of the image. The yellow region marks the most uncertain areas, which are on the boundary between the resection region and the CSF. FIG. 3L is the image with manual segmentation and shows that the human annotator was also unsure regarding this area.

The last row in FIG. 3 (FIGS. 3M-3P) are images showing the different uncertainty thresholds on the resection label. The bottom row shows resection tissue segmentation obtained according to certain embodiments and with different levels of uncertainty thresholds. FIG. 3M has the most uncertain voxels, FIG. 3O has the least uncertain voxels, and FIG. 3N has a number of uncertain voxels between those of FIGS. 3M and 3O. FIG. 3P is the image with manual segmentation. As the uncertain segmentation is reduced from FIG. 3M to FIG. 3N to FIG. 3O, the result better matches the manual annotation in FIG. 3P.

In certain embodiments, a computer-generated segmentation map may be provided jointly with a computer-generated uncertainty map, which can be further facilitated for a fast and interactive selection of personal preferences by the user. The disclosed quantitative results in Tables 1 and 2 and the qualitative results in FIG. 3 demonstrate that the inventive techniques can surpass inter-observer variability, and the user can edit the segmentation according to the uncertainty level.

Exemplary Apparatuses

Figure 4:
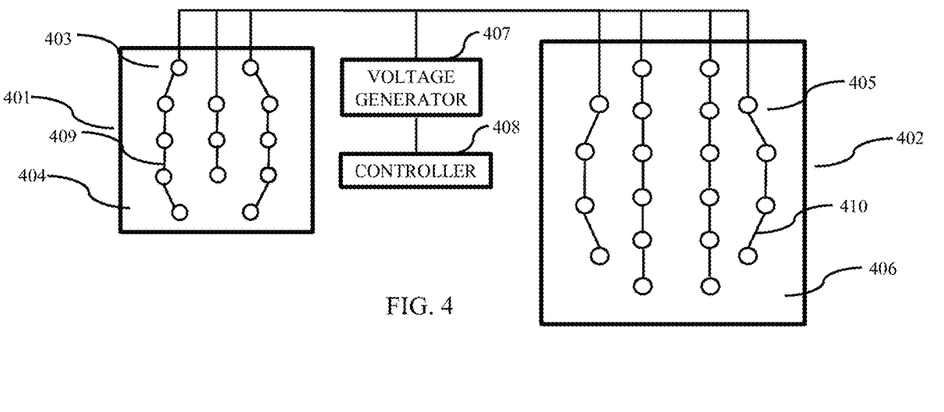
FIG. 4 depicts one example of an apparatus to apply TTFields with modulated electric fields to a subject's body.

FIG. 4 depicts one example of an apparatus to apply TTFields with modulated electric fields to a subject's body. The first transducer 401 includes 13 electrode elements 403, which are positioned on the substrate 704, and the electrode elements 403 are electrically and mechanically connected to one another through a conductive wiring 409. The second transducer 402 includes 20 electrode elements 405, which are positioned on the substrate 406, and the electrode elements 405 are electrically and mechanically connected to one another through a conductive wiring 410. The first transducer 401 and the second transducer 402 are connected to an AC voltage generator 407 and a controller 408. The controller 408 may include one or more processors and memory accessible by the one or more processors. The memory may store instructions that when executed by the one or more processors, control the AC voltage generator 407 to implement one or more embodiments of the invention. In some embodiments, the AC voltage generator 407 and the controller 408 may be integrated in the first transducer 401 and the second transducer 402 and form a first electric field generator and a second electric field generator.

Figure 5:
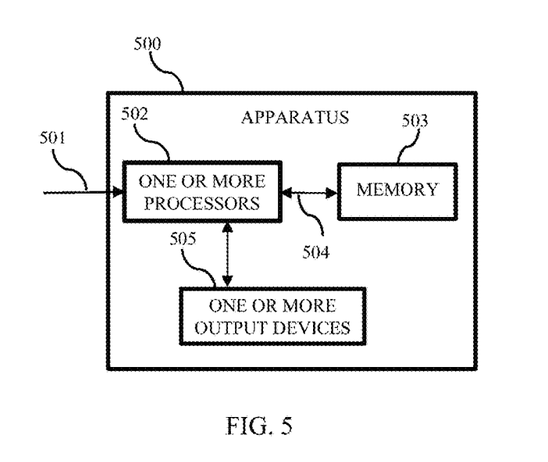
FIG. 5 depicts an example computer apparatus.

FIG. 5 depicts an example computer apparatus for use with the embodiments herein. As an example, the apparatus 500 may be a computer to implement certain inventive techniques disclosed herein. As an example, the apparatus 500 may be a controller apparatus to apply TTFields with modulated electric fields for the embodiments herein. The controller apparatus 500 may be used as the controller 408 of FIG. 4. The apparatus 500 may include one or more processors 502, one or more output devices 505, and a memory 503.

In one example, based on input 501, the one or more processors generate control signals to control the voltage generator to implement an embodiment of the invention. In one example, the input 501 is user input. In another example, the input 501 may be from another computer in communication with the controller apparatus 500. The output devices 505 may provide the status of the operation of the invention, such as transducer selection, voltages being generated, and other operational information. The output devices 505 may provide visualization data according to certain embodiments of the invention.

The memory 503 is accessible by the one or more processors 502 via the link 504 so that the one or more processors 502 can read information from and write information to the memory 503. The memory 503 may store instructions that when executed by the one or more processors 502 implement one or more embodiments of the invention.

Illustrative Embodiments

The invention includes other illustrative embodiments, such as the following.

Illustrative Embodiment 1

A computer-implemented method for tumor segmentation, the method comprises: obtaining image data of a region of interest of a subject's body, wherein the region of interest corresponds to a tumor of the subject's body; generating two or more tumor segmentation predictions based on the image data; calculating a divergence between the two or more tumor segmentation predictions; and generating a visualization of tumor segmentation uncertainty based on the calculated divergence between the two or more tumor segmentation predictions.

Illustrative Embodiment 2

The method of Illustrative Embodiment 1, further comprising resampling the image data to a predetermined resolution.

Illustrative Embodiment 3

The method of Illustrative Embodiment 1, wherein the image data comprises magnetic resonance image (MRI) data.

Illustrative Embodiment 4

An apparatus comprising: one or more processors; and memory storing processor-executable instructions that, when executed by the one or more processors, cause the apparatus to: obtain a training data set of images of other subjects; training two or more segmentation networks using the training set and a unified loss based on a comparison between training outputs of the two or more segmentation networks; and obtain image data of a region of interest of a subject's body, wherein the region of interest corresponds to a tumor of the subject's body; generate two or more segmentation predictions based on the image data and the two or more trained segmentation networks; calculate a divergence between the two or more segmentation predictions; and generate a visualization of tumor segmentation uncertainty based on the segmentation prediction, wherein the visualization of segmentation uncertainty is generated based on a calculated divergence between the two or more segmentation predictions.

Illustrative Embodiment 5

The apparatus of Illustrative Embodiment 4, wherein the memory storing processor-executable instructions that, when executed by the one or more processors, further cause the apparatus to: determine locations on the subject's body to place transducers for applying tumor treating fields based on at least one of the visualization of tumor segmentation uncertainty or the segmentation prediction.

Illustrative Embodiment 6

The apparatus of Illustrative Embodiment 4, wherein the apparatus further comprises a transducer for applying an alternating electric field with predetermined parameters to the subject's body, wherein the alternating electric field is applied based on at least one of the visualization of tumor segmentation uncertainty or the segmentation prediction.

Illustrative Embodiment 7

A computer-implemented method of generating tumor segmentation of a subject's body, the method comprising: obtaining image data of a region of interest, anatomical information, and surgical information of the subject's body, the region of interest corresponding to a postoperative region of a tumor of the subject's body; generating the postoperative tumor segmentation of the subject's body based on the image data, the anatomical information, and the surgical information; and generating a visualization of the region of interest of the subject's body based on the generated postoperative tumor segmentation of the subject's body.

Illustrative Embodiment 8

The method of Illustrative Embodiment 7, wherein the visualization of the region of interest of the subject's body includes uncertainty estimation as to the generated postoperative tumor segmentation of the subject's body.

Embodiments illustrated under any heading or in any portion of the disclosure may be combined with embodiments illustrated under the same or any other heading or other portion of the disclosure unless otherwise indicated herein or otherwise clearly contradicted by context.

Numerous modifications, alterations, and changes to the described embodiments are possible without departing from the scope of the present invention defined in the claims. It is intended that the present invention not be limited to the described embodiments but that it has the full scope defined by the language of the following claims and equivalents thereof.

What is claimed is:

1. A computer-implemented method for tumor segmentation, the method comprises:
   obtaining image data of a region of interest of a subject's body, wherein the region of interest corresponds to a tumor of the subject's body;
   generating two or more tumor segmentation predictions based on the image data using two or more trained segmentation networks;
   calculating a divergence between the two or more tumor segmentation predictions; and
   generating a visualization of tumor segmentation uncertainty based on the calculated divergence between the two or more tumor segmentation predictions.

2. The method of claim 1, further comprising:
   obtaining anatomical information and surgical information of the subject's body, wherein the two or more tumor segmentation predictions are generated based on the image data, the anatomical information, and the surgical information.

3. The method of claim 2, further comprising:
   adding or removing anatomical structures from the visualization based on the anatomical information and surgical information of the subject's body.

4. The method of claim 1, wherein the divergence is calculated through a symmetric Kullback-Leibler (KL) divergence loss.

5. The method of claim 1, wherein the two or more tumor segmentation predictions are generated by segmentation networks, wherein each of the segmentation networks comprises a variational auto-encoder that reconstructs the image data from a shared encoder parameter.

6. The method of claim 1, wherein the visualization comprises an image of the subject with a segmentation prediction and an uncertainty map, wherein the uncertainty map is based on the calculated divergence between the two or more tumor segmentation predictions.

7. The method of claim 6, further comprising:
   removing voxels from the segmentation prediction having an uncertainty greater than a threshold.

8. A computer-implemented method for tumor segmentation, the method comprises
   obtaining two or more segmentation networks trained using a common training set with a plurality of training losses, the common training set comprising images of other subjects;
   obtaining image data of a region of interest of a subject's body, wherein the region of interest corresponds to a tumor of the subject's body;
   generating two or more tumor segmentation predictions based on the image data and the two or more segmentation networks;
   calculating a divergence between the two or more tumor segmentation predictions; and
   generating a visualization of tumor segmentation uncertainty based on the calculated divergence between the two or more tumor segmentation predictions.

9. The method of claim 8, wherein the segmentations networks are trained in parallel using a unified loss, wherein the unified loss comprises at least one of a segmentation loss or a divergence loss.

10. The method of claim 8, further comprising:
applying augmentation to the training data set to obtain an augmented training set, wherein the augmentation comprises at least one of: intensity normalization, random shift, random scale-up of intensity value, random flip, or random scaling of an image patch; and
training the segmentation networks using the augmented training data set.

11. The method of claim 8, further comprising:
obtaining anatomical information and surgical information of the subject's body, wherein the two or more tumor segmentation predictions are generated based on the image data, the two or more trained segmentation networks, the anatomical information, and the surgical information.

12. The method of claim 11, further comprising:
adding or removing anatomical structures from the visualization based on the anatomical information and surgical information of the subject's body.

13. The method of claim 8, further comprising:
determining locations on the subject's body to place transducers for applying tumor treating fields based on at least one of the visualization of tumor segmentation uncertainty or two or more tumor segmentation predictions.

14. An apparatus comprising: one or more processors; and memory storing processor-executable instructions that, when executed by the one or more processors, cause the apparatus to:
obtain a training data set of images of other subjects;
train two or more segmentation networks using the training set and a unified loss based on a comparison between training outputs of the two or more segmentation networks; and
obtain image data of a region of interest of a subject's body, wherein the region of interest corresponds to a tumor of the subject's body;
generate two or more segmentation predictions based on the image data and the two or more trained segmentation networks; and
calculate a divergence between the two or more segmentation predictions; and
generate a visualization of tumor segmentation uncertainty based on the segmentation prediction, wherein the visualization of segmentation uncertainty is generated based on a calculated divergence between the two or more segmentation predictions.

15. The apparatus of claim 14, wherein the unified loss comprises a segmentation loss, a divergence loss, and a reconstruction loss.

16. The apparatus of claim 15, wherein the segmentation loss comprises a Dice coefficient and a cross entropy loss.

17. The apparatus of claim 15, wherein the divergence loss comprises a Kullback-Leibler divergence loss.

18. The apparatus of claim 15, wherein each of the segmentation networks comprises a variational auto-encoder, and the reconstruction loss comprises a reconstruction loss of the variational auto-encoder for each segmentation network.

19. The apparatus of claim 15, wherein the unified loss comprises a parameter to balance the segmentation loss and the divergence loss.

20. The apparatus of claim 14, wherein the memory storing processor-executable instructions that, when executed by the one or more processors, further cause the apparatus to: obtain anatomical information and surgical information of the subject's body, wherein the two or more segmentation predictions are generated based on the image data, the two or more trained segmentation networks, the anatomical information, and the surgical information.

* * * * *